United States Patent [19]

Dubois et al.

[11] 4,112,239
[45] Sep. 5, 1978

[54] MESOGENIC BIPHENYL BENZOATES

[75] Inventors: Jean Claude Dubois; Francoise Barre, both of Paris, France

[73] Assignee: Thomson-CSF, Paris, France

[21] Appl. No.: 647,745

[22] Filed: Jan. 7, 1976

[30] Foreign Application Priority Data

Jan. 10, 1975 [FR] France .................................. 75 00719

[51] Int. Cl.² ........................ C07C 69/76; C07C 69/92
[52] U.S. Cl. ...................................... 560/73; 252/299;
260/404; 260/408; 260/465 D; 350/350;
560/108; 560/141
[58] Field of Search ............... 260/469, 479 R, 473 R,
260/408, 410.5, 476 R; 252/299; 560/73, 108

[56] References Cited

U.S. PATENT DOCUMENTS

| 3,622,619 | 11/1971 | Schoenewalt et al. ...... 260/479 R X |
| 3,660,372 | 5/1972 | Schoenewalt et al. ...... 260/479 R X |
| 3,772,389 | 11/1973 | Lowrance, Jr. ............. 260/479 R X |
| 3,947,375 | 3/1976 | Gray et al. ........................... 252/299 |
| 3,951,846 | 4/1976 | Gavrilovic ........................... 252/299 |
| 3,952,046 | 4/1976 | Scherrer et al. ................. 252/299 X |

OTHER PUBLICATIONS

Savoy, Chemical Abstracts, vol. 42, 1919 (1948).

Primary Examiner—Dolph H. Torrence
Attorney, Agent, or Firm—Oblon, Fisher, Spivak, McClelland & Maier

[57] ABSTRACT

The present invention relates to a family of substances which, in different temperature ranges, exhibit smectic or nematic properties of mesomorphism. Their general formula is:

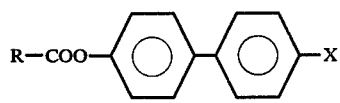

where R designates one of the three radicals:

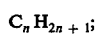

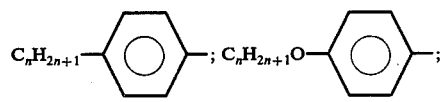

($n$ being a whole number ranging from 1 to 20) and X designatating a halogen (Br preferably) or the nitrile radical C N.

3 Claims, No Drawings

MESOGENIC BIPHENYL BENZOATES

The present invention relates to mesogenic products comprising a substance or a mixture of substances which, within a certain temperature range, exhibit a mesomorphic phase, characteristic of liquid crystal.

The possible applications in display cells, of various liquid crystals, depends upon the nature of their mesomorphism (nematic or smectic in particular), the extent of their temperature range, and different factors such as dielectric anisotropy, coloration and stability.

The mesogenic products in accordance with the invention are stable, colorless, and have a positive dielectric anisotropy in excess of 5. By mixing it is possible to widen and narrow the temperature range exhibited by the substances in the pure state.

According to the invention, there is provided mesogenic products of the general formula:

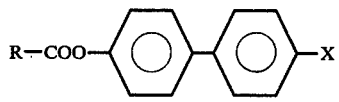
(1)

wherein R belongs to the group of the following three radicals:

$C_nH_{2n+1}-$

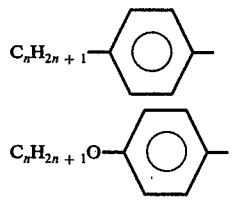

where $n$ is a whole number ranging between 1 and 20; and wherein X belongs to the following group : a halogen and the nitrile radical (C N). A method of manufacturing those products is as follows.

First case : X = Br or Cl

A parabenzophenol ester of the formula :

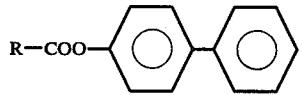
(2)

where R is one of the aforesaid radicals, is bromated (or chlorinated). An ester of this kind itself has been previously obtained in a manner known per se for example by reacting organic acid chloride containing the radical, with parabenzophenol.

In the case of bromide, the parabenzophenol ester reacts at ambient temperature when liquid bromide is poured into a solution of ester and acetic acid. The bromating efficiency is of the order of 50% and yields a compound of the formula:

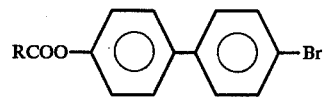
(3)

Second case : X = C N

In a first stage, the operation described in in the first case is performed, yielding the compound formula (3).

In a second stage, the bromide is replaced by the nitrile group in the compound of formula (3). For this purpose, the latter is reacted at 200° C. with cuprous cyanide in the liquid phase (dimethyl formamide).

Example of the first case : X = Br and R = $C_8H_{17}$

Using a known method, a quantity of parabenzophenol nonanoate is prepared :

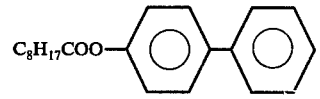

representing 0.06 mols, this being dissolved in a mixture containing 32 milliliters of acetic acid and 16 milliliters of acetic anhydride, in which a small iodine crystal (for example one tenth of a gram) has previously been dissolved. Then at 35° C., a quantity of bromide representing 0.18 mols is poured slowly in. The reaction is allowed to take place for twelve hours at ambient temperature. The precipitate form is filtered off, rinsed in acetic acid and then water. The liquors are concentrated by evaporation using heating, and then refiltered. The precipitates are filtered and recrystallised in ethanol. In this way, 0.35 mols of p'-benzophenol-p-bromononanoate are obtained.

Example of the second case : X = C N and R = $C_8H_{17}$

Using the method described in the previous example, a certain quantity of p'-benzophenol-p-bromo-nonanoate is prepared, 0.025 mols of which are dissolved in a solution containing 0.03 mols of cuprous cyanide in 14 milliliters of dimethylforamide. The reaction is allowed to take place at 200° C. for six hours. Following this, the solution is poured into a mixture containing 25% of ethylene diamine and 75% of water. The product is extracted using ether and then purified by a chromatographic technique on a silica column. The result is 0.008 mols of p'-benzophenol-p-nitrile nonanoate.

The following table sets out the mesomorphism observed in respect of a number of substances specified by the radical X and the radical R contained in the general formula (1) :

| Radical X | Radical R | Mesomorphism observed |
|---|---|---|
| Br | $C_4H_9O-\bigcirc-$ | - smectic from 148° C to 230° C |
| Br | $C_7H_{15}-\bigcirc-$ | - smectic from 133° C to 194° C<br>- nematic from 194° C to 200° C |
| Br | $C_8H_{17}$ | - smectic from 65° C to 100° C |
| CN | $C_7H_{15}-\bigcirc-$ | - nematic from 95.5° C to 230° C<br>(dielectric anisotropy : +8) |
| CN | $C_4H_9O-\bigcirc-$ | - nematic from 120° C to 270° C<br>(dielectric anisotropy : +8) |
| CN | $C_5H_{11}$ | - nematic from 56° C to 72° C<br>(dielectric anisotropy : +10) |
| CN | $C_7H_{15}$ | - nematic by supercooling below 78° C<br>(dielectric anisotropy : +10) |

-continued

| Radical X | Radical R | Mesomorphism observed |
|---|---|---|
| CN | $C_8H_{17}$ | - smectic from 26° or 43.5° to 58° C<br>- nematic from 58° C to 76° C |

Mixtures of the different substances of formula (1), either between one another or with other liquid crystals, make it possible to vary the mesomorphic range.

By way of example, take the following substances:

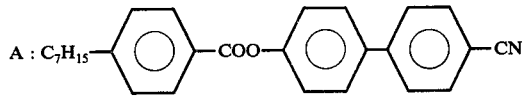

A : $C_7H_{15}$—⬡—COO—⬡—⬡—CN

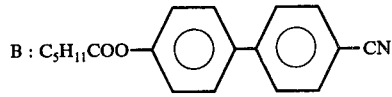

B : $C_5H_{11}COO$—⬡—⬡—CN

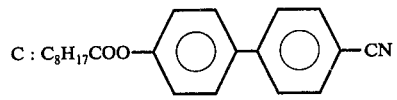

C : $C_8H_{17}COO$—⬡—⬡—CN

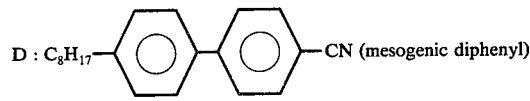

D : $C_8H_{17}$—⬡—⬡—CN (mesogenic diphenyl)

in respect of which the following results have been observed:

| Composition of the mixture (in fractions of mols) | Observed mesomorphism |
|---|---|
| ⅓ A + ⅓ B + ⅓ C | nematic from 24° to 94° C |
| ½ A + ½ B | nematic from 38° C to 111° C |
| ½ C + ½ D | smectic (A) from 12° C to 46° C, nematic from 46° C to 53° C. |

What we claim is:
1. A mesogenic compound of the formula:

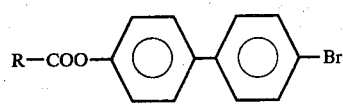

R—COO—⬡—⬡—Br    (1)

wherein R is selected from the group consisting of

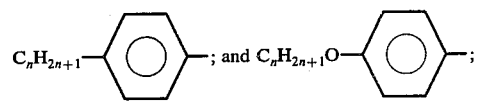

$C_nH_{2n+1}$—⬡—; and $C_nH_{2n+1}O$—⬡—;

and n is a whole number from 1 to 20.

2. A mesogenic compound of the formula:

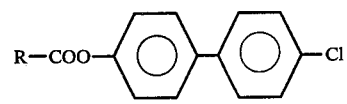

R—COO—⬡—⬡—Cl wherein R is selected from the group consisting of

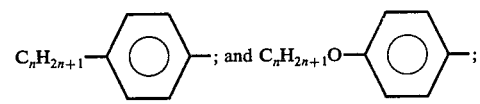

$C_nH_{2n+1}$—⬡—; and $C_nH_{2n+1}O$—⬡—;

and n is a whole number from 1 to 20.

3. The mesogenic compound of claim 1 wherein R is

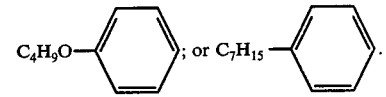

$C_4H_9O$—⬡—; or $C_7H_{15}$—⬡—.

* * * * *